(12) United States Patent
Bonini et al.

(10) Patent No.: US 6,769,568 B2
(45) Date of Patent: Aug. 3, 2004

(54) EQUIPMENT FOR THE MANAGEMENT OF HOSPITAL ACTIVITIES SUCH AS PHARMACEUTICAL TREATMENT

(75) Inventors: Pierangelo Bonini, Peschiera Borromeo (IT); Alberto Sanna, Milan (IT)

(73) Assignee: Diagnostica E Ricerca San Raffaele S.p.A., Milan (IT)

( * ) Notice: Subject to any disclaimer, the term of this patent is extended or adjusted under 35 U.S.C. 154(b) by 31 days.

(21) Appl. No.: 10/297,618

(22) PCT Filed: Jun. 7, 2001

(86) PCT No.: PCT/EP01/06463
§ 371 (c)(1),
(2), (4) Date: Dec. 16, 2002

(87) PCT Pub. No.: WO01/97745
PCT Pub. Date: Dec. 27, 2001

(65) Prior Publication Data
US 2003/0182019 A1 Sep. 25, 2003

(30) Foreign Application Priority Data
Jun. 19, 2000 (IT) ..................................... MI2000A1373

(51) Int. Cl.[7] .............................................. B65G 59/00
(52) U.S. Cl. ......................................... 221/123; 725/78
(58) Field of Search ............................... 221/2, 3, 7, 9, 221/13, 123, 129, 197; 725/74, 78

(56) References Cited

U.S. PATENT DOCUMENTS

| | | |
|---|---|---|
| 4,051,522 A | 9/1977 | Healy et al. .................. 358/86 |
| 4,847,764 A | 7/1989 | Halvorson ................... 364/413 |
| 4,853,521 A | 8/1989 | Claeys et al. ................ 235/375 |
| 4,857,713 A | 8/1989 | Brown ........................ 235/375 |
| 5,036,462 A | 7/1991 | Kaufman et al. ........... 364/413 |
| 5,292,029 A | 3/1994 | Pearson .......................... 221/2 |
| 2003/0140345 A1 * | 7/2003 | Fisk et al. ..................... 725/78 |

FOREIGN PATENT DOCUMENTS

| | | |
|---|---|---|
| DE | 19747353 A1 | 4/1999 |
| EP | 0466492 A2 | 1/1992 |
| WO | WO00/23908 | 4/2000 |

* cited by examiner

*Primary Examiner*—Kenneth Noland
(74) *Attorney, Agent, or Firm*—Jacobson Holman PLLC

(57) ABSTRACT

An equipment for the management of hospital activities as medical tests and pharmacological treatment in conditions of certainty against the mistaking of patients is described. The equipment comprises a bed unit (1) associated with the bed of each patient, at least one cabinet unit (2) associated with every ward and a computerised tray cart (3) that is movable among said units (1, 2). The computerised tray cart (3) comprises a computer (10) provided with display, a reader (11) of computer data connect with said computer (10) and approachable to the bed of the patient for the reading of computer data and their transfer to said computer (10), a plurality of drawers (14–16) with opening controlled by said computer (10), and a printer (17)controlled (10). The bed unit (1) comprises a display (18) connected with a computer for the visualisation of data relative to the patient. The cabinet unit (2) comprises a computer (22), a reader (23) of computer data connected with said computer (23), containing spaces and drawers (24–27) with opening controlled by said computer (22). The computerised tray cart (3), the bed unit (1) and the cabinet unit (2) are connected to each other by a computer network.

3 Claims, 6 Drawing Sheets

EQUIPMENT FOR THE MANAGEMENT OF HOSPITAL ACTIVITIES SUCH AS PHARMACEUTICAL TREATMENT

This is a nationalization of PCT/EP 01/06463, filed Jun. 7, 2001 and published in English.

DESCRIPTION

The present invention concerns an equipment for the management of hospital activities as laboratory tests, pharmacological treatment, dieting and instruments diagnostic that is operating in conditions of certainty against the mistaking of patients and/or of the products destined to it.

One of the greatest risks for patients staying in a hospital or other health care institute consists in the possibility that the data relative to the tests and to the dispensing of drugs are mistaken by error between one patient and the other or that they are not objectively interpreted. Therefore, a different disease that is consequently treated in different way can be diagnosed to a patient affected by a certain disease or, even in the presence of an exact diagnosis, drugs that are suitable for a different disease can be given to him/her.

This problem has been faced in its most general aspects by European patents n. 0491900 and n. 0516782, the first one being specifically addressed to blood tests or other biological samplings, the second being addressed to the dispensing of drugs, the latter term meaning also the dispensing of blood plasma.

Both patents provide for the use of a computer data support that is applied to the patient in such a way that it cannot be removed until the end of hospitalisation, in substance a wrist-band that is fastened to the wrist of the patient. The computer data which are read on the wrist-band with appropriate optical reader allow, in the case of collection and testing of biological samples, to then mark the container of the collected biological sample in a substantially permanent way with the same data, which therefore accompany the same container until the testing laboratory, thus avoiding the mistaking of samples between one patient and the other. In the case of dispensing of drugs the reading of the computer data on the wrist-band, in combination with the reading of additional computer data on a drug container or on the same drug, allows in turn to give the drug that was prescribed for that given patient with absolute certainty.

In European patent n. 0516782 there is also described in general terms the use of a tray cart provided with computer means for the reading, processing and confirm, that can be moved from the patient to the site where the drugs are being dispensed and vice-versa in order to assure the perfect correspondence between the prescribed therapy and the drug being taken.

In the same European patent a possible implementation of a machine is described that is capable to feed, to mark and to fill up with drugs and finally to close drug containers, once again by using computer data corresponding to the ones being read on the wrist-band of the patient.

Nothing is provided instead at the patient's bed, but the presence of a wrist-band that is fastened to the wrist of the same patient.

Scope of the present invention is now to provide an equipment that, by using the teachings provided by the two aforesaid European patents, allows to manage in a complete way the hospital activities of medical tests and pharmacological treatment (extending such concept to dieting) while preventing errors due to the mistaking of patients.

According to the invention such scope is attained with an equipment comprising a computer data support that is fastened to every patient in a substantially permanent way, a bed unit associated with the bed of every patient, at least one cabinet unit associated with each ward and a computerised tray cart that is movable among said units, characterised in that:

a) said computerised tray cart comprises a computer provided with display and mouse control for the processing of computer data, a reader of computer data connected with said computer and movable near the bed of the patient for the reading of computer data and their transfer to said computer, a plurality of drawers with opening controlled by said computer for the housing of containers for biological samples to be collected and of drug containers to be dispensed, a printer controlled by said computer for the printing of labels with computer data corresponding to the ones being read by said reader which are destined to said biological samples containers, and sensors of the patient's vital parameters communicating with said computer;

b) said reading unit comprises a display that is connected with a computer for the visualisation of data relative to the patient, sensors for the detection of data relative to the patient (for instance: presence);

c) said cabinet unit comprises a computer, a computer data reader connected with said computer, spaces and containing drawers with opening controlled by said computer;

d) said computerised tray cart, said bed unit and said cabinet unit are connected with each other by a computer network.

The equipment according to the invention, which is obviously integrable with specific devices and instruments that are considered as being more appropriate each time, allows a safe management of all hospital activities as medical tests and pharmacological treatment and dieting, while eliminating any possibility of error due to the mistaking of patient (including not correct relationing of objective data regarding the patient) from the origin. All data are in fact taken, transmitted, verified and compared via computer without the operator being able to influence the exactness or less of the operation.

The characteristics of the present invention will become evident from the following detailed description of an embodiment thereof, that is illustrated as a non limiting example in the enclosed drawings in which.

Figure 1:
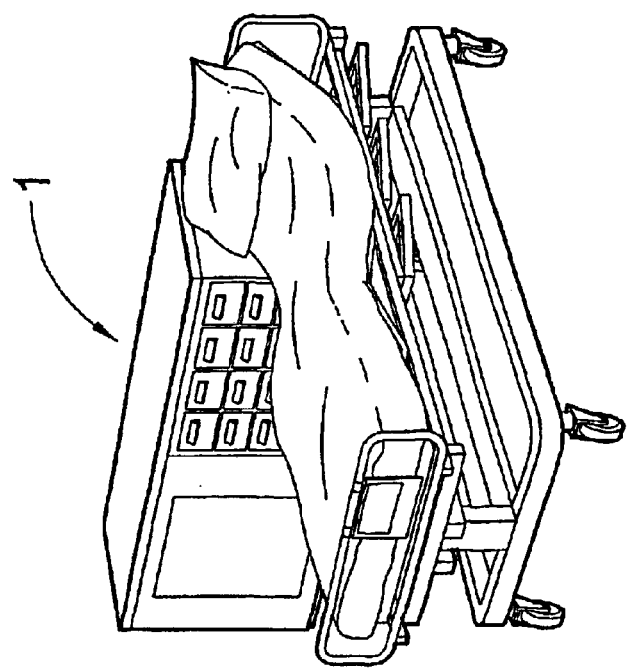
FIG. 1 shows the schematic general assembly of an equipment according to the invention.
Figure 1:
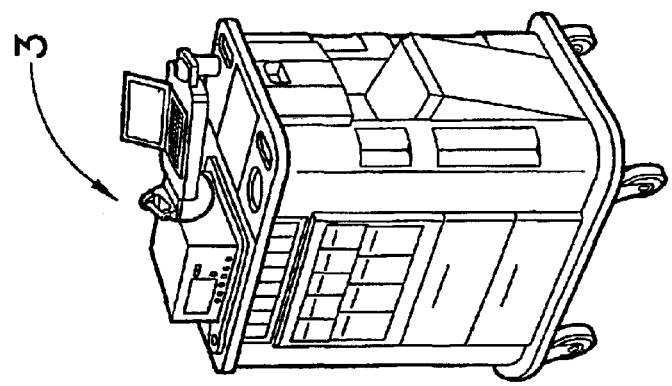
Figure 1:
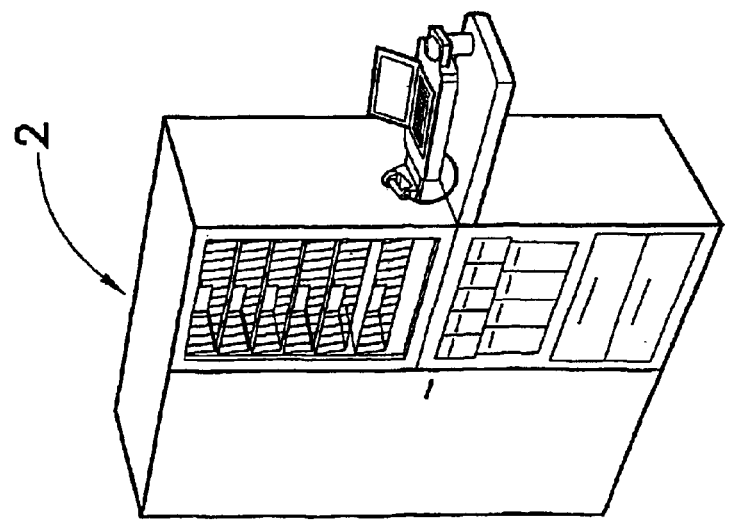
Figure 5:
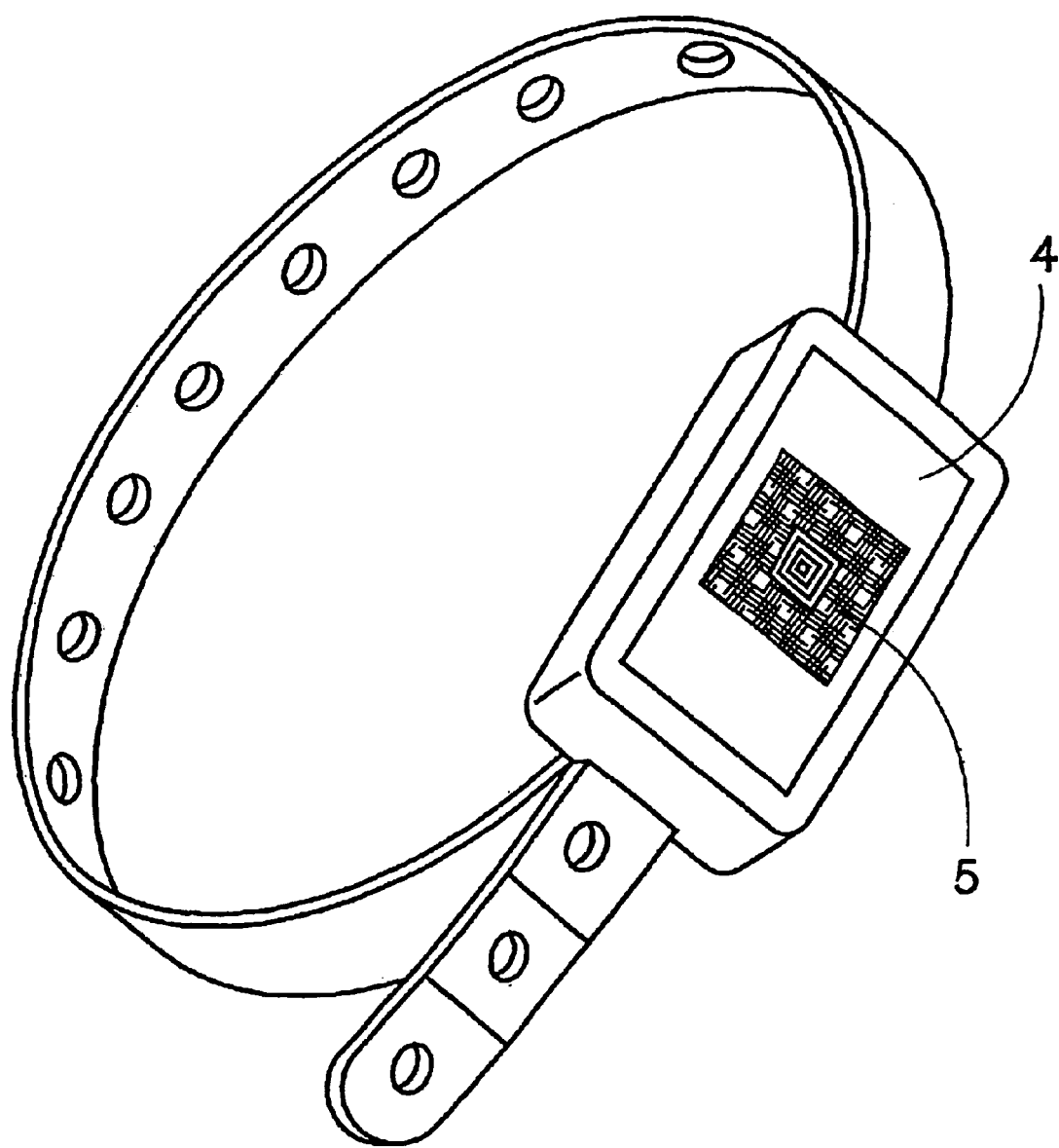
FIG. 5 shows an example of wrist-band for the support of computer data fastenable to the patient.

As schematically shown in FIG. 1, the equipment according to the invention substantially comprises a bed unit 1 for each patient hospitalised in health care institute, at least one cabinet unit 2 for every ward of the health care institute and a computerised tray cart 3 that is movable from one unit to the other. In addition, for each patient, a computer data support permanently associable with the patient is provided, preferably a wrist-band 4 with computer data 5 as shown in FIG. 5.

Figure 2:
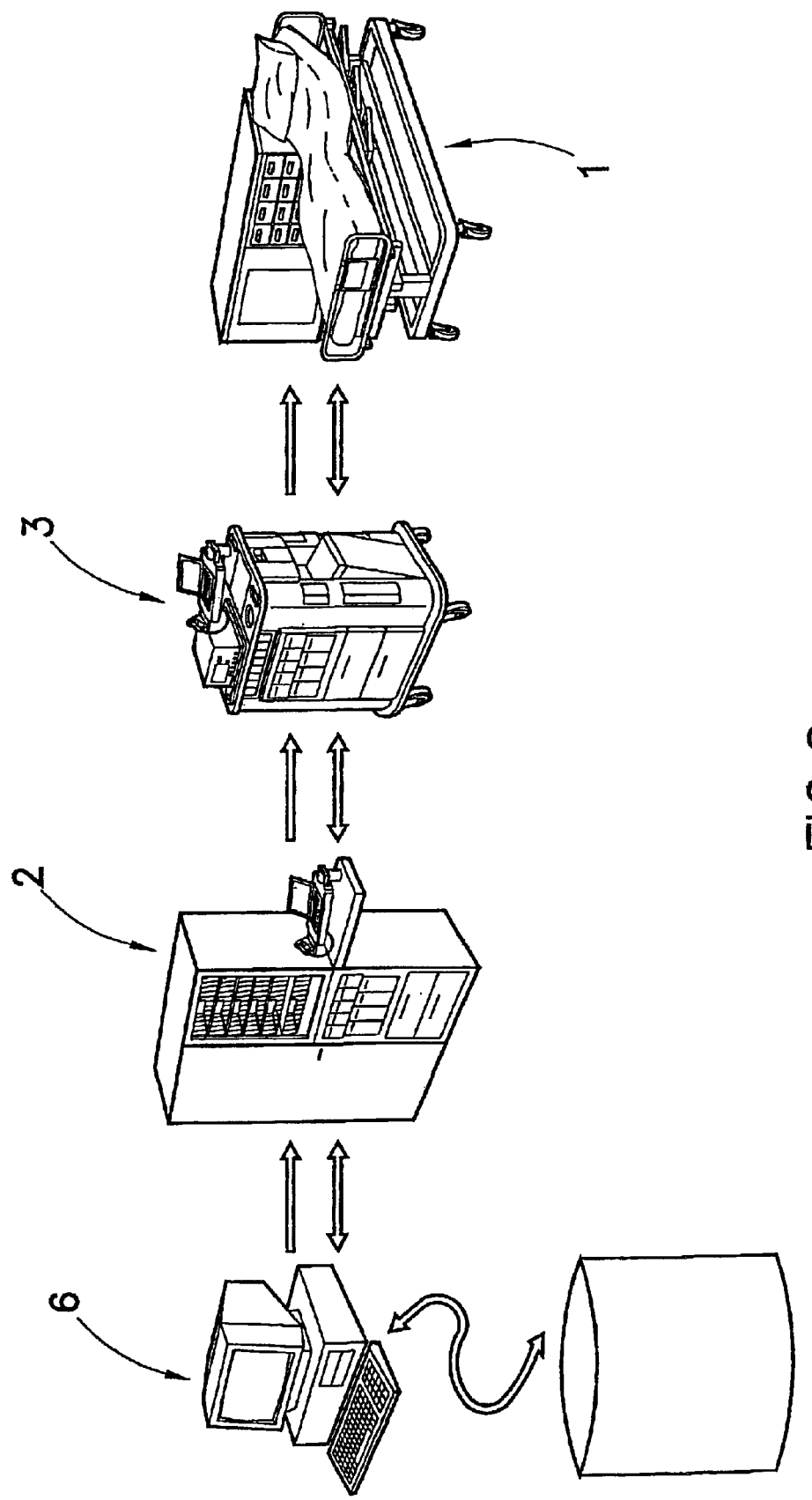
FIG. 2 shows the same equipment completed with a central unit for the supply of drugs.

If the equipment is utilised for the dispensing of drugs, the health care institute can provide for a central unit 6 suitable to supply with drugs several equipments of the ward, as shown in FIG. 2.

Figure 3:
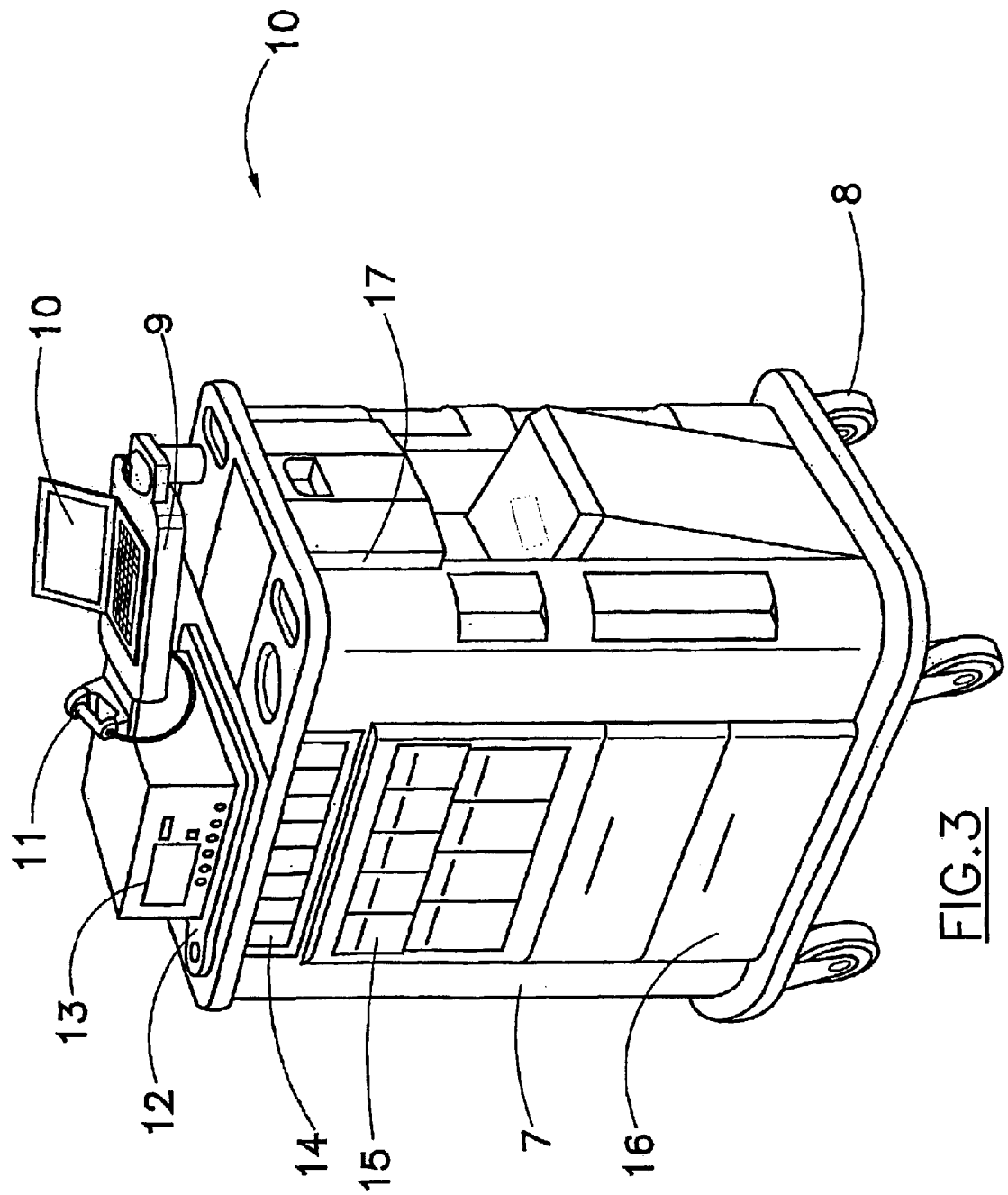
FIG. 3 shows an example of computerised tray cart utilisable in the equipment according to the invention.

The computerised tray cart 3, more clearly illustrated in FIG. 3, is made up of a frame 7 resting on wheels 8, on which a revolving arm 9 can rotate for the support of a portable personal computer 10 with display and mouse control and of an optical reader 11 connected with said computer and provided with wire extension (or other wireless device) in order to allow its movement near the bed of the patient for the reading of the computer data that are memorised on the wrist-band 4 and their transfer to the computer 10.

On the top plane of the frame 7 there is also arranged a revolving arm 12, which supports a device 13, controlled by the computer 10, for the monitoring of the vital parameters of the patient. The device 13 is composed of an additional display and of sensors of the patient's vital parameters such as arterial pressure, oxygen saturation, heart frequency and temperature. The mains power supply is done by means of a easily removable multipolar connector and connected with a supply box. The same is true for the connection with the data network, which can also be obtained through wireless communication.

The body of the frame 7 provides a set of drawers on the front consisting in three rows of drawers 14, 15 and 16, part of which having opening controlled by the computer 10 through actuators and/or indicators and/or sensors; other drawers of the same typology can be present inside other spaces of the tray cart. On one side of the frame 7 a printer 17 for labels is instead provided. Additional components of the tray cart 3, such as containers of clinical charts, containers for syringes and storage spaces of various type, also are provided but not described because of minor interest to the purpose of the invention herein claimed.

Figure 4:
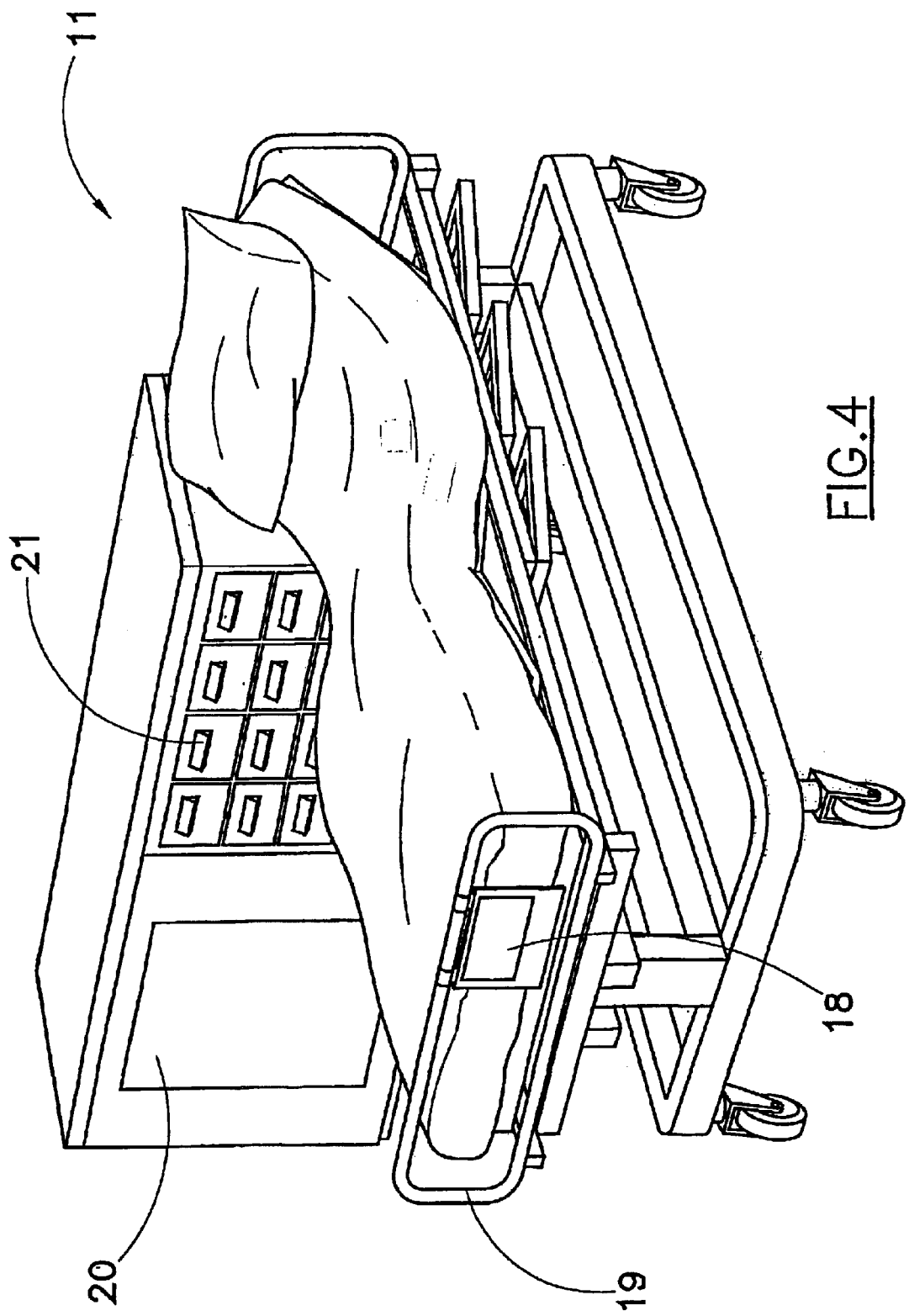
FIG. 4 shows an example of bed unit for the equipment according to the invention.

The bed unit 1, better illustrated in FIG. 4, comprises a display 18 fastened to the foot of the hospitalisation bed 19 and connected via cable or by radio frequency to a computer (not shown) for the visualisation of data relative the patient. In addition sensors (not shown) connected with remote stations are provided in order to detect the presence or less of the patient on the bed. A bedside table 20 can be provided with drawers 21 with traditional opening or controlled by computer according to the same typologies already described for the tray cart.

Figure 6:
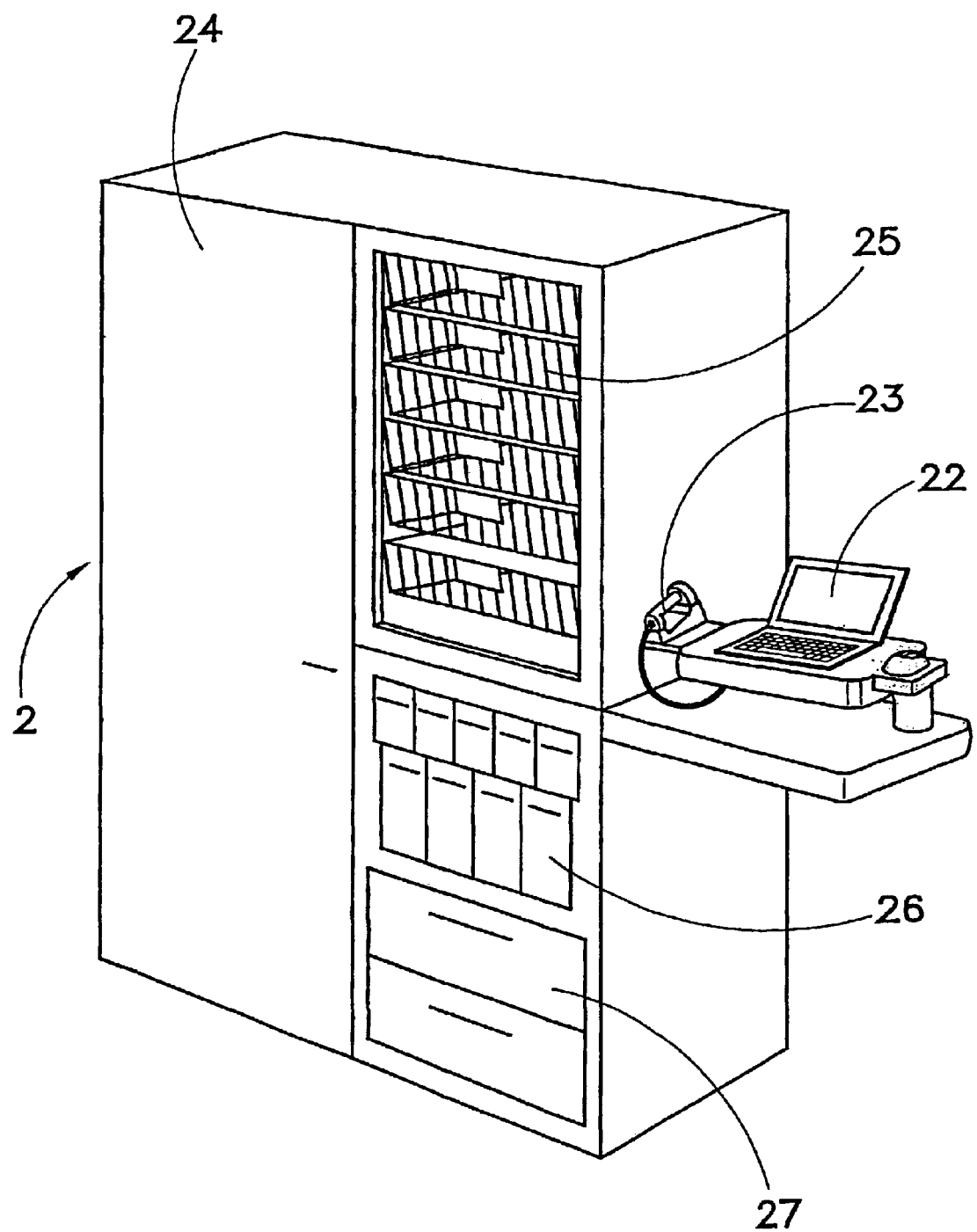
FIG. 6 shows an example of cabinet unit for the equipment according to the invention.

The cabinet unit 2, at least one for unit, better shown in FIG. 6, comprises a portable personal computer 22, an optical reader 23 connected with the computer 22, a space with single door 24 and three groups of drawers 25–27 with traditional opening or controlled by the computer 22 according to the same typologies already provided for the tray cart. There is also provided, even if not shown, a refrigerator unit for the cooling of the space 24 and of the drawers 25–27.

Finally, the computerised tray cart 3, the bed unit 1 and the cabinet unit 2 are connected to each other, and possibly to the central unit 6 for the supply of drugs, by a computer network.

In the sphere of medical testing the equipment according to the invention is utilised as follows. The tray cart 3 is moved near the bed of the patient and the optical reader 11 is pointed onto the wrist-band applied to the patient in order to read the computer data (administrative and/or clinical data, etc.) that are memorised on the same; the reading is communicated to the computer 10. The operator in charge takes one or more containers of biological samples, for instance a test-tube, from one of the drawers of the tray cart that are not necessarily subject to controlled opening and submits the marking present on every container, for instance a label, to reading so as to allow to verify by computer 10 if the container is appropriate for type and characteristics (for instance: product code, batch, expiration). Such reading can possibly be avoided on the basis of precise configuration rules of the software procedures. If the verification gives positive result, the computer 10 enables to operation the printer 17, that prints, and possibly directly applies on each container a label with the patient's data that had previously been read by the reader 11. Then the collection of the biological sample of the patient and its input into the labeled container or containers, that are finally closed and sealed. The previously described modality for the identification and updating of the marker, for instance the printing and application of the label being produced, can be carried out automatically by an appropriate device to which the containers can be fed automatically or manually through a storage of containers.

As an alternative to the above described operating modality, definable as single collection modality, a multiple collection modality can be provided, according to which as many groups of containers as there are patients to be submitted to laboratory testing are prepared, each container of a group is provided with label with the data of the relative patient, etc, and inserted in a sealable casing (for instance one of the controlled opening drawers or other container in turn labelled or otherwise marked with the data of that patient, etc). The tray cart is then brought in proximity of the bed of the first patient, where the reading of the relative wrist-band and of the label is carried out or other marking in case of the use the containers' casing and, if the comparison of the two readings is positive, the actuator/sensor/indicator relative to the opening of the drawer is controlled or else the opening of the casing marked with the same data is authorised for the access to the container to which the collection is destined.

The filled containers, possibly included in envelopes that are sealable by a label issued with the data associated with the activity just being carried out and the remaining ones, are then inserted into a drawer of the tray cart and transferred to the laboratory, where the conveyed information will be duly read through the product labels. If instead the equipment according to the invention is used for the dispensing of drugs, the way it operates is the following.

With the tray cart 3 close to the bed of the patient, the operator in charge through the reader 11 carries out the reading of the computer data of the patient and eventually those of an appropriate label fastened to the print clinical chart of the patient, while verifying the correspondence of the personal identification data. The data relative to the therapy to be followed and therefore to the drugs to be dispensed are therefore communicated through the computer 11, which applies the congruence rules of the pre-set activities and signals to the operator involved the possible not conformity alarms. Such data are generally communicated, according to set rules, to all computers connected by the computer network and to the respective operators.

The tray cart is then carried near the cabinet unit of the ward, where the opening of the drawer of the cabinet that contains the drug to be distributed and the one of a drawer of the tray cart is carried out through computer. The drug is then transferred from a drawer to the other and the two drawers are then closed again. As an alternative, the drug can be introduced in a container sealed by a label with the data of the dispensing (for instance, patient, time, etc.) that is produced by the printer connected with the computer.

The tray cart is then brought back near the bed of the patient, where the reading of the wrist-band of the same patient is carried out and, in case of congruity with the data that are memorised in the computer, the actuator/alert/sensor relative to the opening of the drawer containing the drug to be dispensed is controlled. As an alternative, the reading of the wrist-band of the patient, in conjunction with the reading of the label placed on the sealed container, activates the computer to emit to the operator the authorization for the operation of opening and dispensing to the patient.

The modality just described regarding the drug can also be considered valid for the distribution of meals.

If desired, the same drug can momentarily be inserted in one of the drawers associated with the bedside table near the bed to be then given to the patient at the proper time, still under control given by the computer.

The flow of the drugs from the central unit or central pharmacy 6 to the single cabinets of the ward is finally regulated as follows. The database of the central pharmacy is updated in real time and it communicates with the cabinets of the ward. The drugs are distributed by the central pharmacy to the cabinets of the ward. The information regarding charge and discharge of the cabinets are updated in the database of the pharmacy and in the computers of the cabinets.

What is claimed is:

1. Equipment for the management of hospital activities of medical tests and pharmacological treatment in conditions of certainty against the mistaking of patients, comprising a support (4) for computer data (5) that is attached to each patient in a substantially permanent way, a bed unit (1) associated with the bed of each patient, at least one cabinet unit (2) associated with every ward and a computerised tray cart (3) that is movable between said units (1, 2), characterised in that:

a) said computerised tray cart (3) comprises a computer (10) provided with display and mouse control for the processing of computer data, a reader (11) of computer data connected with said computer (10) and approachable to the bed of the patient for the reading of computer data and their transfer to said computer (10), a plurality of drawers (14–16) with opening controlled by said computer (10) for the housing of containers of biological samples to be collected and of drug containers to be dispensed, a printer (17) controlled by said computer (10) for the printing of labels with computer data corresponding to the ones being read by said reader (11) which are destined to said containers of biological samples, and sensors (13) of physiopathological parameters of the patient communicating with said computer (10), one or more batteries for the supply of the active devices, possibly an electric motor for the movement of the tray cart, a device for the electrical/data connection on board and a device for the electrical/data connection on the ground;

b) said bed unit (1) comprises a display (18) and sensors/actuators/indicators connected with a computer for the visualisation of data relative to the patient;

c) said cabinet unit (2) comprises a computer (22), a reader (23) of computer data connected with said computer (23), containing spaces and drawers (24–27) with opening controlled by said computer (22);

d) said computerised tray cart (3), said bed unit (1) and said cabinet unit (2) are connected to each other by a computer network.

2. Equipment according to claim 1, characterised in that said bed unit (1) comprises in addition sensors of the presence of the patient.

3. Equipment according to claim 1, characterised in that said bed unit (1) comprises in addition a bedside table provided with drawers (21) with opening controlled by means of computer.

* * * * *